Figure 1:
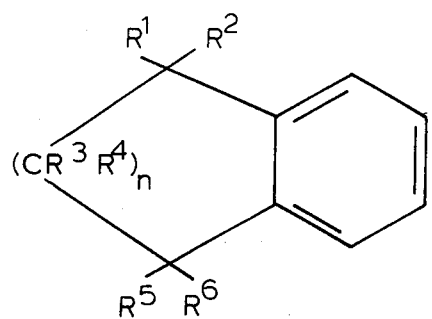

United States Patent [19]

Ferber et al.

[11] Patent Number: 4,515,990
[45] Date of Patent: May 7, 1985

[54] PREPARATION OF INDANES, TETRALINS AND PHENYL ALCOHOL IN FRIEDEL CRAFT REACTION

[75] Inventors: John G. Ferber, Essex; Peter J. Goddard; Robert S. Holden, both of Cheshire, all of England

[73] Assignee: Bush Boake Allen Limited, London, England

[21] Appl. No.: 555,876

[22] PCT Filed: Mar. 11, 1983

[86] PCT No.: PCT/GB83/00074
§ 371 Date: Nov. 7, 1983
§ 102(e) Date: Nov. 7, 1983

[87] PCT Pub. No.: WO83/03247
PCT Pub. Date: Sep. 29, 1983

[30] Foreign Application Priority Data

Mar. 12, 1982 [GB] United Kingdom ............. 8207229

[51] Int. Cl.$^3$ .............................................. C07C 33/34
[52] U.S. Cl. ...................................... 568/808; 568/807
[58] Field of Search ............................ 568/807, 808

[56] References Cited

U.S. PATENT DOCUMENTS 3,856,875 12/1974 Wood ................................. 568/808
4,250,200 2/1981 Wieger et al. .................... 568/808

FOREIGN PATENT DOCUMENTS 0004914 10/1979 European Pat. Off. ......... 568/808
1393449 2/1965 France ............................... 568/808
  63028 1/1932 United Kingdom ............. 568/808
2060680 5/1981 United Kingdom ............. 568/808

Primary Examiner—Werren B. Lone
Attorney, Agent, or Firm—Kane, Dalsimer, Kane, Sullivan and Kurucz

[57] ABSTRACT

An indane, tetralin or phenyl alcohol is made by a heterogeneous, fast, exothermic Friedel Craft reaction and the reaction mixture is cooled to a temperature at which substantial by-product formation is avoided by continuously utilizing the heat of reaction to boil solvent from the reaction mixture. The reaction mixture is generally maintained below atmospheric pressure, typically 20 to 100 mm Hg. The process is of particular value for the production of aryl alcohols by reacting an indane or tetralin with ethylene oxide or propylene oxide.

21 Claims, 3 Drawing Figures

PREPARATION OF INDANES, TETRALINS AND PHENYL ALCOHOL IN FRIEDEL CRAFT REACTION

It is well known to react an aromatic compound with a Friedel Craft reactant in the presence of a Friedel Craft catalyst. The reaction mixture is often heterogeneous, for instance as a result of using aluminium chloride as the complexing agent. The reaction is often exothermic. This is acceptable in many instances but in some instances the reaction is so exothermic and so fast that serious problems can arise. These are accentuated by having a heterogeneous reaction mixture since the solids in the mixture inhibit rapid heat transfer out of the mixture. It is sometimes necessary not only to keep the bulk temperature of the reaction mixture (i.e. the temperature recorded by inserting a thermometer at random locations in the reaction mixture) within controlled limits but it is also necessary to prevent local over heating, on a microscale.

These problems are particularly serious when an indane or tetralin of formula I

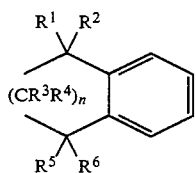

is reacted with an alkylene oxide to form an aryl alcohol of formula II

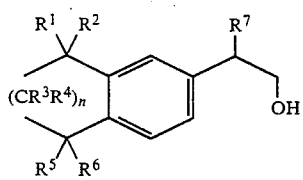

In these formulae $R^1$ to $R^6$ may be the same or different and are selected from hydrogen and alkyl groups having 1 to 4 carbon atoms, n is 1 or 2 and $R^7$ is hydrogen or methyl when the alkylene oxide is ethylene oxide or propylene oxide respectively.

The compounds of formula II are useful perfumery ingredients and they are also useful as intermediates for the production of isochromans, which also are useful perfumery ingredients. For instance a compound of formula II can be reacted with formaldehyde to form an isochroman of formula III

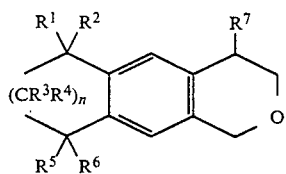

Figure 2:
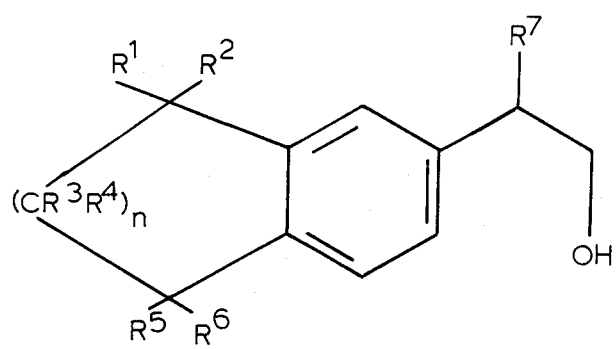
Figure 3:
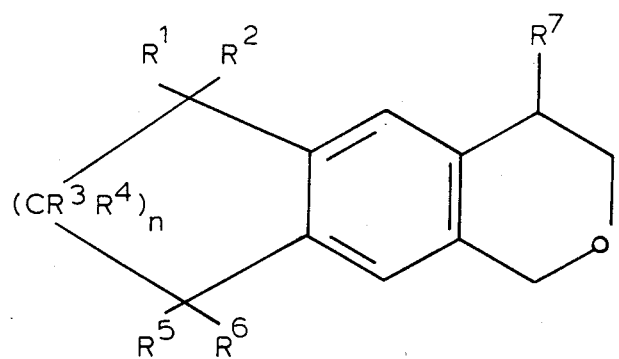

FIGS. 1, 2 and 3 shows formulae for compounds employed in the process of the invention.

The synthesis of a compound of formula II from a compound of formula I is exemplified in U.S. Pat. No. 3,360,530. The reaction is conducted in the presence of excess indane and in the presence of aluminium chloride and using propylene oxide. The reaction is highly sensitive to temperature and it is necessary to ensure that the reaction mixture does not rise above about 20° C. and that local over heating does not occur. Otherwise significant quantities of by-products may occur. However the reaction mixture tends to be viscous and the reaction is very fast and highly exothermic. Accordingly there is a great tendency for the reaction mixture to become too hot and for local over heating to occur.

In U.S. Pat. No. 3,532,719 it is proposed to conduct the reaction in the presence of a halogenated aromatic hydrocarbon solvent, monochlorobenzene, bromobenzene and o-dichlorobenzene being specifically proposed. The alkylene oxide is added slowly to the reaction mixture at a rate that permits adequate cooling, with addition times of 2 to 16 hours being proposed.

In European Patent Publication No. 4914 it is proposed to conduct the reaction in the presence of an alkane having from 5 to 10 carbon atoms, the preferred alkanes being isooctane, n-hexane and n-octane. The alkylene oxide is added with indane to a cold stirred slurry of aluminium chloride in the solvent over a period that, in the examples, is always 2.5 hours or longer.

In laboratory scale operation it is possible, by careful selection of reaction conditions, to operate such processes to give satisfactory yields of the compounds of formula II and low by-product formation. It is necessary to provide good cooling and stirring, but this is possible with small scale apparatus. It is also necessary to perform the reaction at a predetermined rate, such that the cooling that is provided can dissipate the exotherm. In practice the reaction is generally conducted by continuously adding alkylene oxide to the reaction mixture with the result that the amount of heat depends upon the rate of introduction of the alkylene oxide. Accordingly its rate of introduction has to be controlled very accurately having regard to the degree of cooling that is available.

Although satisfactory operation is possible on a laboratory scale it is not possible using simple apparatus on an industrial scale. This is because the size of an industrial reactor means that cooling systems outside the reactor will be inadequate to prevent local over heating, even if there is very aggressive agitation within the reactor. Accordingly it is necessary to provide cooling coils or other cooling systems inside the reactor and to provide also mechanical means for agitating the mixture vigorously. The apparatus therefore has to be complex and expensive, and is made of material that is not corroded by the reaction mixture.

It seems that the by-products that are formed due to over heating in the reaction mixture are associated with cleavage of the cycloaliphatic ring of the indane or tetralin alcohol and the formation of compounds having greater or lesser numbers of carbon atoms than the intended indane or tetralin alcohol. Undesirable tetralin rearrangements to indanes can also occur. Similar problems occur when a compound of formula I is acylated to form the corresponding acyl derivative of the indane or tetralin, using a Friedel Craft system. Likewise, similar problems occur in any Friedel Craft reaction where the reaction mixture contains an indane or tetralin, for instance when an indane or tetralin is formed by ring closure of the cycloaliphatic ring during the reaction.

Problems also arise when benzene (or an alkylbenzene) is reacted with ethylene oxide or other alkylene oxide since the reaction again is fast and highly exothermic and has a tendency for by-product formation if overheating occurs. The by-products in this instance are condensation products between the intended alcohol and the starting material.

It has been our object to devise a method of conducting these heterogeneous, very fast, highly exothermic and temperature sensitive reactions in a way that avoids or minimises the described problems, and in particular unwanted by-product formation, and that permits the reactions to be conducted in good yield using simple apparatus, even on a very large scale.

In the invention a starting aromatic compound is reacted with a Friedel Craft reactant to form an end product selected from indanes, tetralins and phenyl alcohols by a heterogeneous exothermic Friedel Craft reaction in a reaction mixture that contains a Friedel Craft catalyst and a solvent for the reaction and that is cooled to a temperature at which substantial by-product formation is avoided, and the cooling of the reaction mixture throughout the reaction is solely or mainly effected, and local over heating in the reaction mixture is substantially prevented, by continuously utilising the heat of reaction to boil solvent from the reaction mixture.

The reaction is conducted in a reaction vessel. The vessel is generally free of internal cooling coils or other cooling systems. It may be provided with an external cooling jacket, for instance to assist in bringing the reaction mixture to the desired bulk temperature before the reaction starts, but even this is unnecessary. If there is an external cooling system it is generally unnecessary for it to operate during the reaction, although of course it can operate if desired in order to assist maintenance of the desired temperature. The invention is of particular value when applied to industrial scale processes. These can be defined as processes conducted in vessels having a capacity greater than 200 liters, and preferably greater than 500 liters, or as processes when a reaction batch contains at least 50, and generally at least 100 or 150, kg of the starting aromatic compound. Fast, heterogeneous, exothermic industrial scale processes cannot be conducted in a reaction vessel which is only cooled by external cooling means and so, prior to the invention, have always necessitated internal cooling coils. This need is eliminated in the invention.

The main cooling effect during the reaction is caused by the boiling, and in particular this prevents substantial local over heating of the reaction mixture. Boiling solvent from the reaction mixture results in cooling both on a bulk scale and a microscale. Bulk scale cooling arises because as the solvent is evaporated from the mixture it takes out of the mixture its latent heat of evaporation. Accordingly by appropriate selection of the solvent and the pressure and other conditions of the reaction mixture it is possible to maintain the bulk temperature at any chosen value.

Microscale cooling is a particularly important feature of the invention. If the physical conditions have been selected such that boiling maintains the bulk temperature at the desired value if follows that any local exotherm, for instance at the point where alkylene oxide contacts the compound of formula I, will tend to increase the temperature locally and this in turn will inevitably result in increased evaporation of the solvent, and thus increased cooling. Thus the method of the invention has the great advantage that it is self-regulating and that the solvent will boil quicker, and so cause greater cooling, if the exotherm increases either locally or within the bulk reaction mixture. Accordingly, it is not necessary to control the rate of addition of alkylene oxide as accurately as has been essential in the past and, despite this, the risk of local over heating occurring to an extent sufficient to cause by-product formation or reduce yields is prevented.

The method also has the advantage that whereas internally cooled systems must include mechanical agitators to ensure good contact between the reaction mixture and the cooling surfaces mechanical agitation in the invention is relatively unimportant and is not required to ensure adequate cooling. It is generally desirable to provide mechanical agitation, for instance so as to facilitate contact of the reactants, but even this can be less than would normally be required since the boiling inevitably causes agitation.

The solvent that is boiled from the mixture must be selected such that it boils from the reaction mixture when this is at the desired bulk temperature under the prevailing pressure conditions. The reaction mixture is maintained under a pressure at which the liquid medium will commence to boil at the selected bulk temperature.

If the solvent that is to evaporate from the mixture will boil from the mixture at a temperature below the chosen bulk temperature then the reaction mixture must be maintained under elevated pressure. For instance some low molecular weight fluorocarbons may be used best at elevated pressure. If the solvent will boil at atmospheric pressure at the chosen bulk temperature then the reaction mixture may be under atmospheric pressure. Generally however the solvent has a boiling point at atmospheric pressure that is above the desired bulk temperature and the reaction mixture is therefore held at a pressure that is below atmospheric and that is such that the solvent starts to boil at the chosen bulk temperature.

The solvent is normally chosen so that the reaction mixture is maintained at a pressure of 0.5 to 760 mm Hg and most preferably from 0.5 to 500 mm Hg, with pressures of below 100 mm Hg, generally 5 to 100, especially 20 to 100, mm Hg being preferred.

If one of the reactants has a boiling point such that at a convenient pressure, generally a reduced pressure, it will boil at a suitable bulk temperature than an excess of this reactant may be present in the reaction mixture to serve as the solvent. Generally however the reaction mixture will contain an inert solvent. This solvent must be an effective solvent for the reaction, and thus must dissolve or complete the Friedel Craft catalyst to an adequate extent, while leaving a heterogeneous reaction mixture, and must dissolve the starting aromatic compound. The reaction mixture may contain a mixture of solvents. For instance one solvent may be present primarily to solvate one or more of the components of the reaction mixture and the other solvent, which may be less effective at solvating the components, may be present primarily to boil from the reaction mixture during the reaction.

When the end product is an indane or tetralin the bulk temperature is generally below 20° C. The solvent will be chosen such that it will boil at the chosen bulk temperature and pressure. Depending upon the conditions selected from any particular reaction suitable inert solvents may be selected from hydrocarbons, generally aliphatic hydrocarbons containing up to 10 carbon atoms, halogenated hydrocarbons, especially chlorinated and fluorinated aliphatic hydrocarbons containing generally uo to 3 carbon atoms, ethers and nitroalkanes, especially the lower alkyl nitropropanes. Examples of preferred solvents are ethylene dichloride, chloroform, 1 or 2-nitropropane and nitromethane, but dichloromethane is generally particularly preferred since this can easily maintain a bulk temperature of about −15° C. (which is often an optimum temperature) at a pressure of around 20 to 30 mm Hg. Similar solvents may be used for the production of phenyl alcohols but it is generally preferred to rely upon having an excess of the starting aromatic compound, and using this excess as the solvent.

The solvent that is boiled from the mixture is generally condensed by cooling. It may be stored for reuse subsequently but generally is recycled to the reaction mixture, the process then operating as a reflux process. The condensing is generally effected by indirect cooling, the temperature of the coolant being such that it will condense the boiling solvent at the required condenser pressure.

The reaction is generally conducted by gradually adding the alkylene oxide or other Friedel Craft reactant to reaction mixture containing catalyst and solvent, and often also the starting aromatic compound and it is then convenient to add the reactant in a stream containing solvent, for instance solvent that is being recycled to the mixture. For instance the reactant may be discharged beneath the surface of the reaction mixture while surrounded by an annular stream of recycled solvent, so as to ensure that the reactant is diluted by solvent before it contacts the remainder of the reaction mixture. This ability to introduce the reactant in a dilute state, without causing excessive dilution of the reaction mixture is a particular advantage of the invention.

The quantity of inert solvent should be sufficient that the viscosity of the reaction mixture is reduced to a satisfactory level but should not be so great as to increase the volume of the reaction mixture undesirably. Generally it is between 1 and 30, preferably 1 to 10, moles per mole of starting aromatic compound.

The reaction is generally conducted by gradually adding the alkylene oxide or other Friedel Craft reactant to the reaction mixture, whereupon instantaneous reaction of the alkylene oxide with the starting aromatic compound occurs. Accordingly the duration of the reaction is controlled by the time taken to add the alkylene oxide to the reaction mixture. Whereas times of 2½ up to 12 hours are typical in the prior art, because of the need to give time to dissipate the exotherm, in the invention the duration of the addition of the amount of alkylene oxide necessary for complete reaction can be completed in less than 2 hours, often 0.25 to 1.75 hours.

The Friedel Craft catalyst is preferably aluminium chloride but others are known, for instance triethyl and other alkyl aluminiums and ferric chloride, and any other solid complexing agent that will cause the desired reaction to occur may be used. When the end product is an alcohol or a ketone the catalyst will form a complex with it and may more accurately be described as a complexing agent.

When the end product is an alcohol or ketone the molar ratio Friedel Craft reactant:Friedel Craft catalyst is generally about 1:0.7–1.7, preferably about 1:1–1.5, most preferably about 1:1.1–1.3, and the molar ratio Friedel Craft reactant:starting aromatic compound is generally about 1:0.8–5, preferably about 1:1–3, most preferably about 1:1.1–1.5 unless the aromatic compound is to serve also as solvent in which event the ratio is generally about 1:2–30, preferably about 1:3–10.

When the end product is a hydrocarbon the molar ratios aromatic compound:Friedel Craft catalyst:Friedel Craft reactant is generally about 1:0.05–0.5:0.8–2, preferably about 1:0.1–0.3:1–1.5, most preferably about 1:0.2:1.1–1.5.

The invention is particularly surprising and advantageous, especially when considering the difficulties associated with prior art methods, when applied to the synthesis of an aryl alcohol of formula II by reaction of an indane or tetralin of formula I with ethylene oxide or, preferably, propylene oxide. The bulk temperature is generally in the range −50° to +10° C., preferably −30° to 0° C. and most preferably −20° to −10° C. The pressure is generally in the range 20 to 70 mm Hg and the solvent is preferably dichloromethane.

The preferred starting aromatic compounds are therefore the indanes and tetralins of formula I.

The preferred indanes are pentamethyl indane (n=1, $R^1$ to $R^6$ are each methyl and $R^4$ is hydrogen), and trimethylmonoethyl indane (n=1, $R^1$, $R^2$ and $R^4$ are methyl, $R^3$ and $R^6$ are hydrogen and $R^5$ is ethyl) or a mixture of these compounds such as may be obtained by the reaction of iso-amylene and α-methylstyrene, for instance as described in European Patent Publication No. 0061267. A preferred tetralin for use in the invention is the compound in which n=2, $R^3$ and $R^4$ are hydrogen and $R^1$, $R^2$, $R^5$ and $R^6$ are methyl. The preferred end products of the invention are the corresponding compounds of formula II wherein $R^7$ is methyl.

The compound of formula I is generally included in the reaction vessel with the catalyst before adding any alkylene oxide but if desired some or all of it may be added with the alkylene oxide. The alkylene oxide may be introduced into the vapour space above the liquid phase but preferably is introduced below the surface of the liquid phase.

The compound of formula II is obtained in the reaction as a complex with the catalyst. The complex may be broken, and the non-complexed alcohol separated, as described in, for instance U.S. Pat. No. 3,532,719 or European Patent Publication No. 4914. Preferably the complex is worked up by discharging it into water and allowing the aqueous and organic phases to separate. This causes hydrolysis of the complex in an exothermic reaction. The rate of discharge of the product into water should be regulated so as to ensure that, under the pressure prevailing over the water, the solvent is not lost by evaporation.

The separated organic phase may be purified by further washing and subsequent distillation in order to remove any unreacted indanes or tetralins and the solvent material together with smaller quantities of by-products including chlorohydrins.

The aryl alcohol reaction products find use as intermediates in the synthesis of isochromans by their reaction with formaldehyde or a precursor thereof. The aryl alcohol complex may be reacted directly with a formaldehyde precursor as is described in U.S. Pat. No. 3,532,719 and European Patent Publication No. 4914. The noncomplexed aryl alcohol may be reacted with formaldehyde without any separation of solvent, unreacted indanes or tetralins or by-products or may be purified as outlined above. Preferably at least the solvent is removed prior to the reaction with formaldehyde. Any unreacted indane or tetralin is unchanged by this further reaction and may therefore be removed from the final isochroman product during the purification of that product.

Another advantageous group of compounds that can be made by the invention are the acyl derivatives of indanes and tetralins of formula I, the preferred compounds again being as described above. The acyl derivatives are obtained by using, as the Friedel Craft reactant, an appropriate acylating agent, preferably acetic anhydride or acetyl chloride. The reaction may be conducted generally as described in European Patent Publication No. 4914 or U.S. Pat. No. 3,246,044 but modified by continuously boiling from the reaction mixture an appropriate inert solvent (generally ethylene dichloride or dichloromethane) and by maintaining the pressure such that the bulk temperature is generally in the range −50° to 10° C., preferably −30° to 0° C. and most preferably −20° to −10° C. With the named solvents this generally necessitates a pressure of 20 to 100 mm Hg. The process is however applicable and useful in any heterogeneous, highly exothermic, Friedel Craft reaction between an aromatic compound and a Friedel Craft reactant tht forms an end product that is an indane, tetralin or phenyl alcohol. The aromatic compound may be an aromatic hydrocarbon or a halogenated hydrocarbon or may be an aromatic hydrocarbon substituted by an alkyl group that can be converted during the reaction to a carbonium intermediate. The Friedel Craft reactant may be an alkylene oxide, an acylating agent, or an alkene, generally having a chain of at least 3 carbon atoms, usually 3, 4 or 5 carbon atoms and usually having the double bond either in a terminal position or adjacent to a terminal position.

The starting reactant may be selected from indanes and tetralins and the Friedel Craft reactant may be selected from ethylene oxide, propylene oxide, acetyl chloride and acetic anhydride, in which event the end product is the corresponding ethyl or propyl alcohol derivative or acetyl derivative of the indane or tetralin. Such reactions are preferably conducted at temperatures below 20° C., as discussed above.

Alternatively the reaction may effect ring closure to form an indane or tetralin from an appropriate aromatic compound. This compound may be a benzylic halide or a 1-halo-2-aryl-alkane (wherein the halogen is selected from chlorine or bromine) or a tertiary carbonium ion formed in situ from an alkyl group substituted on an aromatic compound, and the Friedel Craft reactant may be an appropriate alkene that will ring close with the aromatic compound to form the desired indane or tetralin. For instance the aromatic compound may be 2-chloro-2-phenyl (or alkyl substituted phenyl) propane and the alkene may be an alkene having terminal unsaturation and 3 to 6 carbon atoms, generally neohexene. Alternatively the starting aromatic compound may be 1-chloro-2-methyl-2-phenyl (or alkyl phenyl) propane and the alkene may be a but-2-ene. In these reactions the solvent that is boiled is preferably dichloromethane or ethylene dichloride. An example of the reaction where a tertiary carbonium ion is formed in situ arises when the reaction mixture contains an alkyl group substituted on an aromatic compound (for instance 2-phenyl(or methyl phenyl)-propane and also contains tertiary butyl chloride and neohexene or other appropriate alkene. Neohexene can serve as the solvent that is to be boiled from the mixture but preferably the mixture contains also dichloromethane or ethylene dichloride. All these reactions are generally conducted below 20° C., preferably −50° to +10° C. and most preferably −30° to 0° C. Descriptions of suitable processes, apart from the cooling step of the invention, are to be found in U.S. Pat. Nos. 3,246,044 and 3,856,875, Japanese 79125647 and Netherlands 7802038.

A third class of processes according to the invention are those involving the reaction of an aromatic hydrocarbon with an alkylene oxide to form an appropriate phenyl alcohol. The aromatic hydrocarbon is generally benzene but may be toluene or ethyl benzene. The alkylene oxide is generally ethylene oxide but may be propylene oxide. The solvent that is boiled from the reaction mixture is generally excess benzene or other aromatic starting compound. The reaction is generally conducted at a temperature below 40° C. but above the melting point of the aromatic compound, for instance 5° to 40° C. The pressure may be between 30 and 100 mm Hg. The formation of phenyl ethyl alcohol by this method is described by Kirk-Othmer in Encyclopedia of Chemical Technology, 3rd Edition, Vol. 3, page 789 and the conditions described the references cited in that may be utilised, subject to the modification that the reaction mixture is cooled by reducing the pressure and distilling the benzene.

The invention is illustrated by the following examples:

EXAMPLE 1

1,1,2,3,3-pentamethyl indane, containing 9% 1,1,3-trimethyl-3-ethyl indane and precursors (564 gm 3 moles) in dichloromethane (300 ml) are charged to a 3 liter flask, fitted with mechanical stirrer, a sintered reagent delivery tube and a dry-ice condensor (total cooling surface area 0.1 square meter). The solution is cooled to −15° C. by application of an acetone-dry-ice bath and powdered aluminium chloride (401 g, 3 moles) is added. The pressure is reduced to a value of 20 to 30 mm Hg such that the dichloromethane refluxes gently at −15° C. No external cooling was applied. Propylene oxide (174.5 g, 3 moles) in dichloromethane (300 ml), at ambient temperature, is added over 1 hour to the rapidly stirred reaction medium through the sintered delivery tube opening into the reaction vessel beneath the liquid level. The reaction temperature is maintained at −15° C. throughout the addition and the reaction exotherm is dissipated solely by reflux through the dry-ice condensor, which is maintained at −78° C. with dry-ice and acetone. After stirring for a further 5 minutes at −15° C., the product complexes in solution are discharged to a 5 liter brine cooled jacketed vessel containing 1500 ml water initially at 2° C. This operation takes 10 minutes with the hydrolysis temperature reaching a maximum of 40° C. After settling, the two phases are separated and the oil layer washed three times with saturated brine. The solvent is removed using a rotary evaporator and the resulting oil fractionated under 2 mm Hg vacuum using a 1 foot vigreux column to give mainly two bulked fractions namely recovered indanes (95% by g.l.c.) and 1,1,2,3,3-pentamethyl-5-($\beta$-hydroxyisopropyl)indane and isomeric trimethyl ethyl ($\beta$-hydroxyisopropyl)indanes (98% by g.l.c.).

70% of the indane charge was converted. Theory yield on converted indane was 89%. Theory yield on propylene oxide was 62%..

EXAMPLE 2

The reaction is conducted as in Example 1 except that neat propylene oxide (175 g) is added during 2 hours to the 3 liter flask that contains indanes (564 g), aluminium chloride (401 g) and dichloromethane (1173 g) and that is maintained at −15° C.

66% of the indane charge was converted. Theory Yield on converted indane was 88%. Theory yield on propylene oxide was 58%.

The refluxing dichloromethane contained no detectable propylene oxide, demonstrating instantaneous reaction of the added (volatile) propylene oxide.

EXAMPLE 3

The process of example 2 is repeated on an industrial scale, using a standard 300 gallon glass lined mild steel vessel. The yield based on propylene oxide varies between 53–58%, the yield based on converted indane is 80–90% and the conversion of indane varies between 60–70%.

EXAMPLE 4 (COMPARATIVE)

The procedure of Example 3 is repeated but with the plant modified such that the reaction is not conducted under reflux, cooling is applied via the jacket only but the bulk temperature is maintained at −15° C. over the 8–10 hours required for the propylene oxide addition. The yields on propylene oxide were reduced to 33–37%, the yields based on converted indane are 30–40% and the conversion of indane varies between 70–85%. The crude product contains significant quantities of disproportionated indanes.

EXAMPLE 5

2-chloro-2(4'-methylphenyl)propane is reacted with neohexene in the presence of aluminium chloride to form 1,1,3,4,4,6-hexamethyltetralin in accordance with the general technique described in U.S. Pat. No. 3,246,044 except that the reaction is conducted in the presence of ethylene dichloride and the reaction mixture is held at a temperature of about −15° C. by reducing the pressure to 10 mm Hg and boiling the ethylene dichloride from the mixture.

EXAMPLE 6 p-cymene is reacted with t-butylchloride, neohexene and a mixture of aluminium chloride and triethylaluminium to form 1,1,3,4,4,6-hexamethyl tetralin by the general process described in U.S. Pat. No. 3,856,875 or Japanese 79125647 but modified by cooling the reaction mixture by including dichloromethane in it and refluxing this from the mixture at about 20 mm Hg, thereby maintaining a reaction temperature of about −15° C.

EXAMPLE 7

1-chloro-2-methyl-2(4'-methyl phenyl)propane is reacted with 2-methyl-but-2-ene and aluminium chloride to form 1-isopropy-2,3,3,5-tetramethyl indane by the general process described in Netherlands Patent Application No. 7802038 except that maintenance of the desired reaction temperature at about −15° C. is achieved by including dichloromethane in the reaction mixture and reducing the pressure to around 20 to 30 mm Hg, the bulk temperature then being about −15° C.

EXAMPLE 8

1,1,2,3,3,6-hexamethyl indane is reacted with acetyl chloride in the presence of aluminium chloride to form 7-acetyl 1,1,3,4,4,6-hexamethyl-1,2,3,4-tetrahydronaphthalene using the general process described in European Patent Publication No. 4914 or U.S. Pat. No. 3,246,044 modified in that the reaction mixture is cooled solely by including in the reaction mixture ethylene dichloride or dichloromethane and by reducing the pressure in the reaction vessel to 10 to 30 mm Hg and thereby refluxing the solvent from the reaction mixture and maintaining a temperature of around −15° C.

EXAMPLE 9

An excess of benzene is mixed with aluminium chloride in a reaction vessel to which ethylene oxide is fed while maintaining the pressure in the vessel at about 50 mm Hg and refluxing benzene from the reaction mixture, thereby maintaining a temperature around 6°–10° C. The product of the reaction is phenethyl alcohol.

What is claimed is:

1. In a process for reacting a starting aromatic compound selected from the group consisting of indanes, tetralins, benzylic halides, 1-halo-2-aryl-alkanes, tertiary alkyl-substituted compounds, benzene and $C_{1-4}$alkyl-substituted benzenes with a Friedel Craft reactant selected from the group consisting of ethylene oxide and propylene oxide when the aromatic compound is selected from indanes, tetralins, benzene and alkyl-substituted benzenes; from the group consisting of acetyl chloride and acetic anhydride when the aromatic compound is selected from indanes and tetralins; and from the group consisting of alkenes when the aromatic compound is selected from benzylic halides, 1-halo-2-aryl-alkanes and tertiary alkyl-substituted compounds to form an end product selected from indanes, tetralins and phenyl alcohols by a heterogeneous exothermic Friedel Craft reaction in a reaction mixture that contains a Friedel Craft catalyst and a solvent for the reaction and that is cooled to a temperature at which substantial by-product formation is avoided and that is below 40° C., the improvement which comprises; in that cooling of the reaction mixture throughout the reaction is solely or mainly effected, and local over heating in the reaction mixture is substantially prevented, by continuously utilizing the heat of reaction to boil solvent from the reaction mixture.

2. A process for reacting a starting aromatic compound selected from indanes and tetralins to make an end product selected from ethyl alcohol, propyl alcohol and acetyl derivatives of indanes and tetralins by reaction with a Friedel Craft reactant selected from ethylene oxide, propylene oxide, acetyl chloride and acetic anhydride by a heterogeneous exothermic Friedel Craft reaction mixture that contains a Friedel Craft catalyst and a solvent for the reaction, and in which the reaction mixture is cooled and is maintained at a temperature below 20° C. at which substantial by-product formation is avoided, and local over-heating in the reaction mixture is substantially prevented, by continuously utilizing the heat of reaction to boil the solvent from the reaction mixture.

3. A process according to claim 2 in which the starting aromatic compound is a compound of formula I

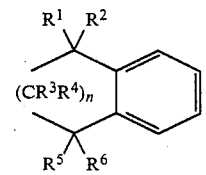

the end product is a compound of formula II

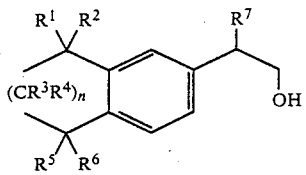

(wherein, in both formulae, $R^1$ to $R^6$ may be the same or different and represent hydrogen or $C_{1-4}$ alkyl, n is 1 or 2 and, in formula II, $R^7$ is hydrogen or methyl), the Friedel Craft reactant is ethylene oxide or propylene oxide and the reaction temperature is maintained below 20° C. by boiling the solvent from the reaction mixture.

4. A process according to claim 1 in which the starting reactant is selected from benzylic halides and 1-halo-2-aryl-alkanes, wherein the halogen is selected from chlorine or bromine, and carbonium compounds that can be formed in situ from a tertiary alkyl group substituted on an aromatic compound, the Friedel Craft reactant is an alkene and the end product is an indane or tetralin and the reaction temperature is maintained below 20° C. by boiling the solvent from the reaction mixture.

5. A process according to claim 2 in which the reaction temperature is maintained by the boiling at $-30°$ to 0° C.

6. A process according to claim 2 in which the solvent is selected from dichloromethane and ethylene dichloride.

7. A process according to claim 1 in which the starting reactant is benzene or benzene optionally substituted by $C_{1-4}$ alkyl and the Friedel Craft reactant is ethylene oxide or propylene oxide and the end product is 1-hydroxy-2-phenyl ethanol or propanol wherein the phenyl group may be optionally substituted by alkyl and the reaction temperature is between the melting point of the starting aromatic compound and 40° C.

8. A process according to claim 2 in which the solvent has a boiling point, at atmospheric pressure, above the bulk temperature of the reaction mixture and the reaction mixture is held at a pressure that is below atmospheric and that is such that the solvent boils from the reaction mixture at the bulk temperature.

9. A process according to claim 2 conducted at a pressure of 5 to 100 mm Hg.

10. A process according to claim 3 conducted at a temperature of $-30°$ to 0° C. and a pressure of 20 to 100 mm Hg and using propylene oxide as the Friedel Craft reactant.

11. A process according to claim 3 conducted at a temperature of $-30°$ to 0° C. and a pressure of 20 to 100 mm Hg and using propylene oxide as the Friedel Craft reactant and using dichloromethane as the solvent.

12. A process according to claim 3 in which the compound of formula II is selected from pentamethyl indane and trimethylmonoethyl indane and mixtures thereof, conducted at a temperature of $-30°$ to 0° C. and a pressure of 20 to 100 mm Hg and using propylene oxide as the Friedel Craft reactant.

13. A process according to claim 2 in which the Friedel Craft catalyst comprises aluminium chloride.

14. A process according to claim 2 in which the solvent that is boiled from the reaction mixture is condensed by cooling and is recycled to the reaction mixture.

15. A process according to claim 1 characterised in that the reaction is conducted by gradually adding the Friedel Craft reactant to the reaction mixture and by the fact that the addition is completed in less than 2 hours.

16. A process according to claim 2 conducted in a vessel having a volume above 200 liters that is free of any internal cooling means.

17. A process for reacting a compound of the formula

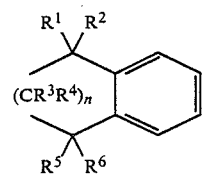

wherein $R^1$ to $R^6$ may be the same or different and represent hydrogen or $C_{1-4}$ alkyl, n is 1 or 2; to make a compound selected from the group consisting of pentamethyl indane and trimethylmonoethyl indane and mixtures thereof; with a propylene oxide by a heterogeneous exothermic Friedel Craft reaction in a reaction mixture that contains a Friedel Craft catalyst and dichloromethane solvent and a solvent for the reaction, and in which the reaction mixture is cooled and conducted at a temperature of $-30°$ to 0° C. and a pressure of 20 to 100 mm Hg at which substantial by-product formation is avoided, and local over-heating in the reaction mixture is substantially prevented, by continuously utilizing the heat of reaction to boil the solvent from the reaction mixture.

18. A process according to claim 1 characterized in that the reaction is conducted by gradually adding the Friedel Craft reactant to the reaction mixture and by the fact that the addition is completed in less than 2 hours.

19. A process according to claim 2 characterized in that the reaction is conducted by gradually adding the Friedel Craft reactant to the reaction mixture and by the fact that the addition is completed in less than 2 hours.

20. A process according to claim 3 characterized in that the reaction is conducted by gradually adding the Friedel Craft reactant to the reaction mixture and by the fact that the addition is completed in less than 2 hours.

21. A process according to claim 17 characterized in that the reaction is conducted by gradually adding the propylene oxide reactant to the reaction mixture and by the fact that the addition is completed in less than 2 hours.

* * * * *